US012014812B2

(12) United States Patent
Miyamoto et al.

(10) Patent No.: US 12,014,812 B2
(45) Date of Patent: Jun. 18, 2024

(54) MEDICAL IMAGE DISPLAY CONTROL DEVICE, METHOD, AND PROGRAM FOR DISPLAYING MEDICAL IMAGES WITH SELECTABLE TABS

(71) Applicant: FUJIFILM Corporation, Tokyo (JP)

(72) Inventors: Masaki Miyamoto, Tokyo (JP); Takuma Okuno, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/326,261

(22) Filed: May 20, 2021

(65) Prior Publication Data

US 2021/0278939 A1 Sep. 9, 2021

Related U.S. Application Data

(63) Continuation of application No. PCT/JP2019/035379, filed on Sep. 9, 2019.

(30) Foreign Application Priority Data

Nov. 22, 2018 (JP) .................... 2018-219464

(51) Int. Cl.
*G16H 30/20* (2018.01)
*G06F 3/0482* (2013.01)
(Continued)

(52) U.S. Cl.
CPC .......... *G16H 30/20* (2018.01); *G06F 3/0482* (2013.01); *G06F 3/0483* (2013.01); *G16H 10/60* (2018.01);
(Continued)

(58) Field of Classification Search
CPC ........ G16H 40/67; G16H 40/20; G16H 10/60; G16H 15/00; G16H 30/20; G16H 30/40;
(Continued)

(56) References Cited

U.S. PATENT DOCUMENTS 8,225,199 B2 7/2012 Okubo et al.
9,019,301 B2 4/2015 Matsue et al.
(Continued)

FOREIGN PATENT DOCUMENTS

CN 101053521 10/2007
CN 101527135 9/2009
(Continued)

OTHER PUBLICATIONS

"International Search Report (Form PCT/ISA/210) of PCT/JP2019/035379," dated Dec. 10, 2019, with English translation thereof, pp. 1-5.

(Continued)

*Primary Examiner* — Justin R. Blaufeld
(74) *Attorney, Agent, or Firm* — JCIPRNET

(57) ABSTRACT

A medical image display control device includes a reception unit that receives an input instruction, a creation unit that creates a display image having a tab and a viewer region in which at least a medical image is displayed, the creation unit creating a new display image having a tab and a viewer region different from a viewer region of a display image displayed on a display unit based on the input instruction received by the reception unit, a display controller that performs control such that the tab of the new display image created by the creation unit and the already displayed tab are displayed so as to be selectable on the display unit, and a switching display controller that performs control such that in a case where any tab of the tabs displayed on the display unit is selected, the viewer region corresponding to the selected tab is switched with the already displayed viewer region and is displayed on the display unit.

18 Claims, 9 Drawing Sheets

(51) Int. Cl.
  *G06F 3/0483* (2013.01)
  *G16H 10/60* (2018.01)
  *G16H 15/00* (2018.01)
  *G16H 30/40* (2018.01)
  *G16H 40/20* (2018.01)
  *G16H 40/67* (2018.01)

(52) U.S. Cl.
  CPC ............ *G16H 15/00* (2018.01); *G16H 30/40* (2018.01); *G16H 40/20* (2018.01); *G06F 2203/04803* (2013.01); *G16H 40/67* (2018.01)

(58) Field of Classification Search
  CPC .................. G06F 3/0482; G06F 3/0483; G06F 2203/04803
  See application file for complete search history.

(56) References Cited

U.S. PATENT DOCUMENTS

| | | | | |
|---|---|---|---|---|
| 9,342,145 | B2 | 5/2016 | Moffett | |
| 9,892,475 | B1* | 2/2018 | Ephrat | G16H 50/20 |
| 2004/0024303 | A1* | 2/2004 | Banks | A61B 6/566 |
| | | | | 600/407 |
| 2004/0193650 | A1* | 9/2004 | Funahashi | G16H 30/20 |
| 2005/0111621 | A1* | 5/2005 | Riker | G16H 20/40 |
| | | | | 378/65 |
| 2007/0186189 | A1* | 8/2007 | Schiller | G06F 16/54 |
| | | | | 715/205 |
| 2007/0237380 | A1* | 10/2007 | Iwase | G16H 30/40 |
| | | | | 382/131 |
| 2008/0044069 | A1* | 2/2008 | DuGal | G06T 7/0012 |
| | | | | 382/128 |
| 2008/0089584 | A1* | 4/2008 | VanMetter | G06T 11/00 |
| | | | | 382/173 |
| 2008/0126982 | A1* | 5/2008 | Sadikali | G16H 50/70 |
| | | | | 715/810 |
| 2008/0167902 | A1* | 7/2008 | Baba | G16H 15/00 |
| | | | | 705/3 |
| 2008/0168474 | A1* | 7/2008 | Jeon | G06F 9/4843 |
| | | | | 719/320 |
| 2009/0073114 | A1* | 3/2009 | Bay | G06F 3/0482 |
| | | | | 345/156 |
| 2009/0129642 | A1* | 5/2009 | Matsumoto | G06T 5/50 |
| | | | | 382/128 |
| 2010/0223573 | A1* | 9/2010 | Tanaka | A61B 6/563 |
| | | | | 715/802 |
| 2011/0231766 | A1* | 9/2011 | Chao | H04N 1/387 |
| | | | | 715/810 |
| 2012/0284657 | A1* | 11/2012 | Hafey | G16H 30/20 |
| | | | | 715/765 |
| 2012/0296962 | A1* | 11/2012 | Tada | G16H 30/20 |
| | | | | 709/203 |
| 2013/0088512 | A1* | 4/2013 | Suzuki | G16H 10/60 |
| | | | | 345/629 |
| 2013/0293694 | A1* | 11/2013 | Mizobe | H04N 7/183 |
| | | | | 348/77 |
| 2013/0308839 | A1* | 11/2013 | Taylor | G16H 30/20 |
| | | | | 382/128 |
| 2013/0326405 | A1* | 12/2013 | Nord | G06F 3/048 |
| | | | | 715/810 |
| 2014/0098931 | A1* | 4/2014 | Profio | A61B 6/03 |
| | | | | 345/1.3 |
| 2014/0133632 | A1* | 5/2014 | Wakai | A61B 6/44 |
| | | | | 378/98 |
| 2014/0156307 | A1* | 6/2014 | Masuda | G16H 30/20 |
| | | | | 705/3 |
| 2015/0086092 | A1* | 3/2015 | Itada | G06F 18/40 |
| | | | | 382/128 |
| 2015/0347464 | A1* | 12/2015 | Takata | G16H 50/00 |
| | | | | 707/728 |
| 2016/0192991 | A1* | 7/2016 | Vahala | A61N 7/02 |
| | | | | 600/407 |
| 2017/0124771 | A1* | 5/2017 | Canfield | G06T 19/20 |
| 2017/0220748 | A1* | 8/2017 | Okabe | G16H 30/40 |
| 2018/0218785 | A1* | 8/2018 | Sugiyama | A61B 6/037 |
| 2020/0050405 | A1* | 2/2020 | Achiwa | G06F 3/0673 |

FOREIGN PATENT DOCUMENTS

| | | | | |
|---|---|---|---|---|
| CN | 103941855 | | 7/2014 | |
| JP | 2006061278 | | 3/2006 | |
| JP | 2006262977 | | 10/2006 | |
| JP | 2007293521 | | 11/2007 | |
| JP | 2007293521 | A * | 11/2007 | |
| JP | 2012110465 | A * | 6/2012 | ........... A61B 5/0013 |
| JP | 2013021459 | | 1/2013 | |
| JP | 2018121823 | | 8/2018 | |
| WO | 2009113429 | | 9/2009 | |

OTHER PUBLICATIONS

"Written Opinion of the International Searching Authority (Form PCT/ISA/237) of PCT/JP2019/035379," dated Dec. 10, 2019, with English translation thereof, pp. 1-10.

Office Action of Japan Counterpart Application, with English translation thereof, dated Jun. 14, 2022, pp. 1-7.

"Office Action of China Counterpart Application", issued on Nov. 3, 2023, with English translation thereof, p. 1-p. 15.

"Office Action of China Counterpart Application No. 201980077023.3", issued on Apr. 12, 2024, p. 1-p. 12.

* cited by examiner

MEDICAL IMAGE DISPLAY CONTROL DEVICE, METHOD, AND PROGRAM FOR DISPLAYING MEDICAL IMAGES WITH SELECTABLE TABS

CROSS-REFERENCE TO RELATED APPLICATIONS

This application is a Continuation of PCT International Application No. PCT/JP2019/035379 filed on Sep. 9, 2019, which claims priority under 35 U.S.C § 119(a) to Japanese Patent Application No. 2018-219464 filed on Nov. 22, 2018. Each of the above application(s) is hereby expressly incorporated by reference, in its entirety, into the present application.

BACKGROUND OF THE INVENTION

1. Field of the Invention

The present disclosure relates to a medical image display control device, method, and program.

2. Description of the Related Art

In recent years, as medical devices such as computed tomography (CT) devices and magnetic resonance imaging (MRI) devices have advanced, it has been possible to perform image diagnosis using higher quality medical images with high resolution. In particular, since a region of a lesion can be accurately specified by image diagnosis using CT images and MR images, appropriate treatment has been performed based on the specified results.

The medical image is analyzed by computer-aided diagnosis (CAD) using a discriminator in which learning is performed by deep learning, and a region, a position, and a volume of the lesion included in the medical image are extracted, and the extracted region, position, and volume are acquired as analysis results. As described above, an analysis result generated by analysis processing is stored in association with inspection information such as a patient's name, gender, and age, and a modality from which the medical image is acquired in a database, and is provided for diagnosis. A radiologist interprets the medical image on his or her interpretation terminal device while referring to the distributed medical image and the analysis result, and creates an interpretation report.

In a case where the interpretation of the medical image is performed, a list of medical images to be interpreted is sent to an interpretation terminal. The list includes the aforementioned inspection information. In a case where an inspection to be interpreted is selected from the list displayed on the interpretation terminal, the medical image acquired in the selected inspection is displayed.

However, in a case where the medical image of the inspection selected from the list is displayed on a screen, only the medical image of the inspection selected from the list can be usually displayed on one screen. Thus, for example, in a case where it is desired to compare and observe the medical image acquired in the past and the medical image acquired in the current inspection for the same patient, the display on the screen needs to be switched and observed by sequentially selecting the past and the current inspections from the list, and thus, there is a problem in that it is difficult to observe the medical image.

Thus, WO2009/113429A discloses a technology capable of simultaneously displaying medical images of a plurality of inspections in an easy-to-see manner by generating a screen which can be moved, enlarged, and reduced as a separate screen independent of a main screen on which the medical image acquired in the current inspection is displayed and displaying the medical image acquired in the past on this separate screen.

SUMMARY OF THE INVENTION

In the technology described in WO2009/113429A, the generated separate screen needs to be moved to an easy-to-see position, enlarged, or reduced, which requires time and effort of an operation by a user. Since sizes of the main screen and the separate screen are different, it may be difficult to observe the medical image, for example, in a case where comparison display is performed.

The present disclosure has been made in view of the above circumstances, and an object of the present invention is to improve the efficiency of an operation by facilitating observation of a medical image and reducing the time and effort of an operation by a user.

A medical image display control device of the present disclosure includes a reception unit that receives an input instruction, a creation unit that creates a display image having a tab and a viewer region in which at least a medical image is displayed, the creation unit creating a new display image having a tab and a viewer region different from a viewer region of a display image displayed on a display unit, based on the input instruction received by the reception unit, a display controller that performs control such that the tab of the new display image created by the creation unit and the already displayed tab are displayed so as to be selectable on the display unit, and a switching display controller that performs control such that in a case where any tab of the tabs displayed on the display unit is selected, the viewer region corresponding to the selected tab is switched with the already displayed viewer region and is displayed on the display unit.

In the medical image display control device of the present disclosure, the viewer region may include an image display region in which the medical image is displayed and at least one or more regions of a patient information region in which information regarding a patient is displayed, an inspection list region in which information regarding each inspection is displayed for each inspection, a thumbnail display region in which the medical image acquired in one inspection is reduced and displayed, or a toolbar region in which a plurality of input instruction buttons are displayed.

The medical image display control device of the present disclosure may further include a switching unit that switches between whether or not to apply image processing on the same medical image to be displayed on a first tab to the same medical image to be displayed in a selection of a tab other than the first tab in a case where the same medical image is displayed in a selection of any tab of a plurality of tabs.

In the medical image display control device of the present disclosure, in a case where the reception unit receives an input instruction related to two or more medical images, the creation unit may create the new display images, each including a viewer region in which the two or more medical images are displayed so as to be comparable.

In the medical image display control device of the present disclosure, in a case where the reception unit receives an input instruction related to an image series including a plurality of medical images acquired in one inspection, the creation unit may create the new display images, each including a viewer region in which the plurality of medical images of the image series are displayed by a predetermined number of images, the number of the new display images corresponding to the plurality of medical images.

In the medical image display control device of the present disclosure, in a case where a snapshot function of storing the viewer region in a state in which a display state is restorable is provided, and the viewer region is stored by the snapshot function, the creation unit may create a new display image including the stored viewer region.

In the medical image display control device of the present disclosure, the creation unit may create a display image having identification information for identifying the medical image to be displayed in the viewer region on the tab corresponding to the viewer region.

In this case, the identification information may include a mark associated with each medical image. The identification information may include character information indicating information related to the medical image.

A medical image display control method of the present disclosure includes receiving an input instruction, creating a new display image having a tab and a viewer region different from a viewer region of a display image having a tab and a viewer region in which at least a medical image is displayed which is displayed on a display unit, based on the received input instruction, displaying the tab of the created new display image and the already displayed tab so as to be selectable on the display unit, and performing control such that in a case where any tab of the tabs displayed on the display unit is selected, the viewer region corresponding to the selected tab is switched with the already displayed viewer region and is displayed on the display unit.

A program causing a computer to execute the medical image display control method according to the present disclosure may be provided.

Another medical image display control device according to the present disclosure includes a memory that stores instructions to be executed by a computer, and a processor that is configured to execute the stored instructions. The processor executes processing of receiving an input instruction, creating a new display image having a tab and a viewer region different from a viewer region of a display image having a tab and a viewer region in which at least a medical image is displayed which is displayed on a display unit, based on the received input instruction, displaying the tab of the created new display image and the already displayed tab so as to be selectable on the display unit, and performing control such that in a case where any tab of the tabs displayed on the display unit is selected, the viewer region corresponding to the selected tab is switched with the already displayed viewer region and is displayed on the display unit.

According to the medical image display control device, method, and program of the present disclosure, it is possible to improve the efficiency of the operation by facilitating observation of the medical image and reducing the time and effort of the operation by the user.

DESCRIPTION OF THE PREFERRED EMBODIMENTS

Figure 1:
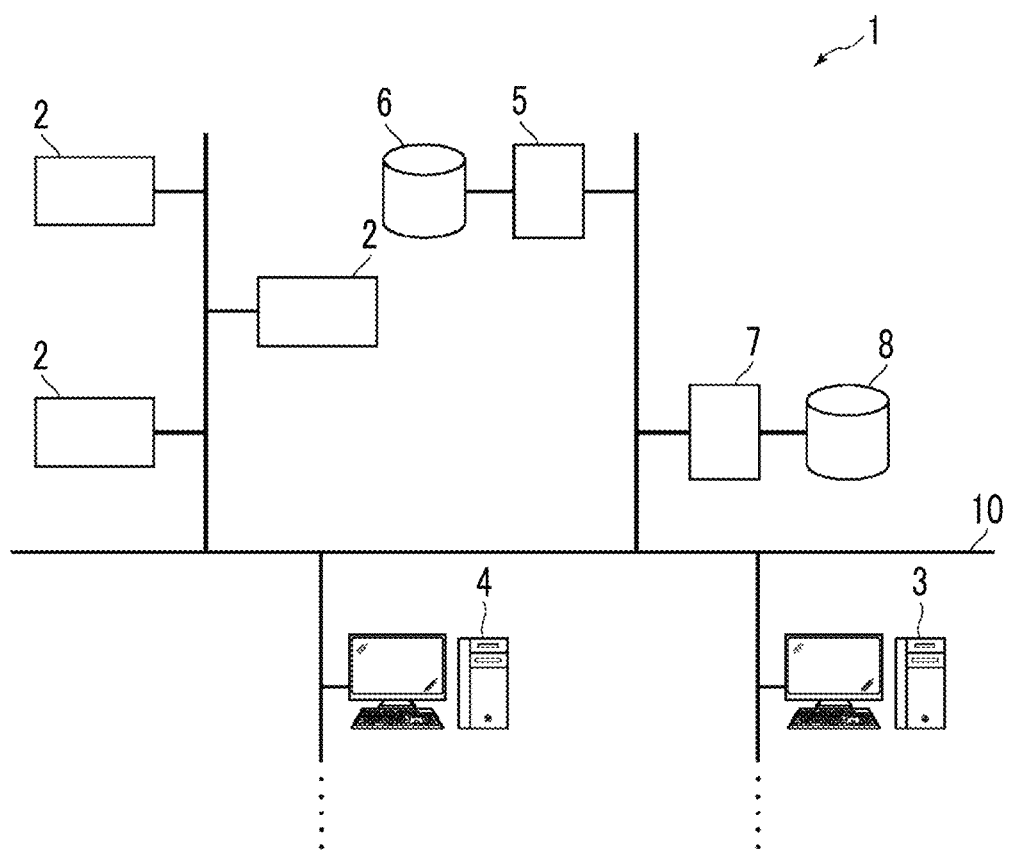
FIG. 1 is a diagram showing a schematic configuration of a medical information system to which a medical image display control device according to an embodiment of the present disclosure is applied.

Hereinafter, embodiments of the present disclosure will be described with reference to the drawings. FIG. 1 is a diagram showing a schematic configuration of a medical information system to which a medical image display control device according to a first embodiment of the present disclosure is applied. The medical information system 1 shown in FIG. 1 is a system configured to capture an inspection target portion of a patient which is a subject based on an inspection order from a doctor in a clinical department using a known ordering system, store a medical image acquired by the capturing, perform interpretation by a radiologist and creation of an interpretation report, and perform browsing of the interpretation report by the doctor in the clinical department as a requesting party and detailed observation of the medical image to be interpreted.

As shown in FIG. 1, the medical information system 1 is configured such that a plurality of modalities 2, a plurality of interpretation workstations (WSs) 3 which are interpretation terminals, clinical department workstations (WSs) 4, a medical information management server 5, a medical information database 6, an interpretation report server 7, and an interpretation report database 8 are connected in order to communicate with each other via a network 10.

Each device is a computer on which an application program for functioning as a component of the medical information system 1 is installed. The application program is recorded and distributed on a recording medium such as a digital versatile disc (DVD) or a compact disc read-only memory (CD-ROM), and is installed on the computer from the recording medium. Alternatively, the application program is stored in a storage device of a server computer connected to a network or a network storage in a state of being accessible from the outside, and is downloaded and installed on the computer according to a request.

The modality 2 is a device that acquires a medical image representing a diagnosis target portion by capturing a portion as a diagnosis target of the subject. Specifically, the modality is a CT device, an MRI device, a positron emission tomography (PET) device, or a computed radiography (CR) device.

The interpretation WS 3 is a computer that is used by the radiologist of the medical image for the interpretation of the medical image and the creation of the interpretation report, and includes a processing device, a high-definition display unit, and input units such as a keyboard and a mouse. The interpretation WS 3 includes the medical image display control device according to the present embodiment. The medical image display control device according to the present embodiment will be described later. In the interpretation WS 3, each processing such as a browsing request for the medical image to the medical information management server 5, various kinds of image processing on the medical image received from the medical information management server 5, display of the medical image, support of the creation of the interpretation report, a registration request and a browsing request for the interpretation report to the interpretation report server 7, and display of the interpretation report received from the interpretation report server 7 is performed by executing a software program for each processing. Since the processing other than the processing performed by the medical image display control device of the present embodiment is performed by a well-known software program, detailed description thereof is omitted herein.

The clinical department WS 4 is a computer to be used by the doctor in the clinical department for the detailed observation of the image, browsing of the interpretation report, and creation of an electronic medical record, and includes a processing device, a display unit such as a high-definition display, and input devices such as a keyboard and a mouse. In the clinical department WS 4, each processing of a browsing request for medical information to the medical information management server 5, display of the image received from the medical information management server 5, a browsing request of the interpretation report to the interpretation report server 7, and display of the interpretation report received from the interpretation report server 7 is performed by executing a software program for each processing.

The medical information management server 5 is a device on which a software program for providing a function of a database management system (DBMS) to a general-purpose computer is installed. The medical information management server 5 has a large-capacity storage included in the medical information database 6. This storage may be a large-capacity hard disk device connected to the medical information management server 5 by a data bus, or may be a disk device connected to a network-attached storage (NAS) and a storage area network (SAN) connected to the network 10. In a case where a registration request for the medical information such as the medical image from the modality 2 is received, the medical information management server 5 prepares the medical image in a database format, and registers the medical image in the medical information database 6.

In a case where the browsing request for the medical image from the interpretation WS 3 and the clinical department WS 4 is received via the network 10, the medical information management server 5 searches for the medical image registered in the medical information database 6, and transmits the searched medical image to the interpretation WS 3 and the clinical department WS 4 as a requesting party.

In the medical information database 6, image data of the medical image acquired in the modality 2 is registered. Inspection information is added as accessory information to the medical image. The accessory information may include, for example, an image ID (identification) for identifying an individual medical image, a patient ID for identifying the patient, an inspection ID for identifying an inspection, an inspection date and an inspection time at which the medical image is generated, a type of the modality used in the inspection for acquiring the medical image, patient information such as a patient's name, age, and gender, an inspection portion (imaging portion), imaging information (imaging protocol, imaging sequence, imaging method, imaging condition, and use of contrast agent), and information of a series number or a collection number in a case where a plurality of medical images are acquired in one inspection. In a case where the plurality of medical images are acquired in one inspection, the plurality of medical images may be acquired by a different modality 2. For example, one inspection may acquire both a CT image and an MRI image.

In the medical information database 6, an analysis result for the medical image is registered as medical information. The analysis result for the medical image may be an analysis result acquired in the interpretation WS 3 to be described later, but may be an analysis result acquired in an analysis device provided separately from the interpretation WS 3 and connected to the network 10. In a case where the medical image can be analyzed in the clinical department WS 4, the analysis result for the medical image may be an analysis result acquired in the clinical department WS 4.

The interpretation report server 7 incorporates the software program for providing the function of the database management system (DBMS) to the computer. In a case where a registration request for the interpretation report from the interpretation WS 3 is received, the interpretation report server 7 prepares the interpretation report in a database format, and registers the interpretation report in the interpretation report database 8.

For example, an interpretation report in which information such as an image ID for identifying the medical image to be interpreted, a radiologist ID for identifying the radiologist who performs interpretation, a lesion name, positional information of a lesion, a medical opinion, and a degree of certainty of the medical opinion is recorded is registered in the interpretation report database 8.

As described above, the interpretation WS 3 includes the medical image display control device 9 according to the present embodiment. Thus, a medical image display control program of the present embodiment is installed on the interpretation WS 3. The medical image display control program is recorded and distributed on a recording medium such as a DVD or a CD-ROM, and is installed on the computer constituting the interpretation WS 3 from the recording medium. Alternatively, the medical image display control program is stored in a storage device of a server computer connected to a network or a network storage in a state of being accessible from the outside, and is downloaded and installed on the computer.

Figure 2:
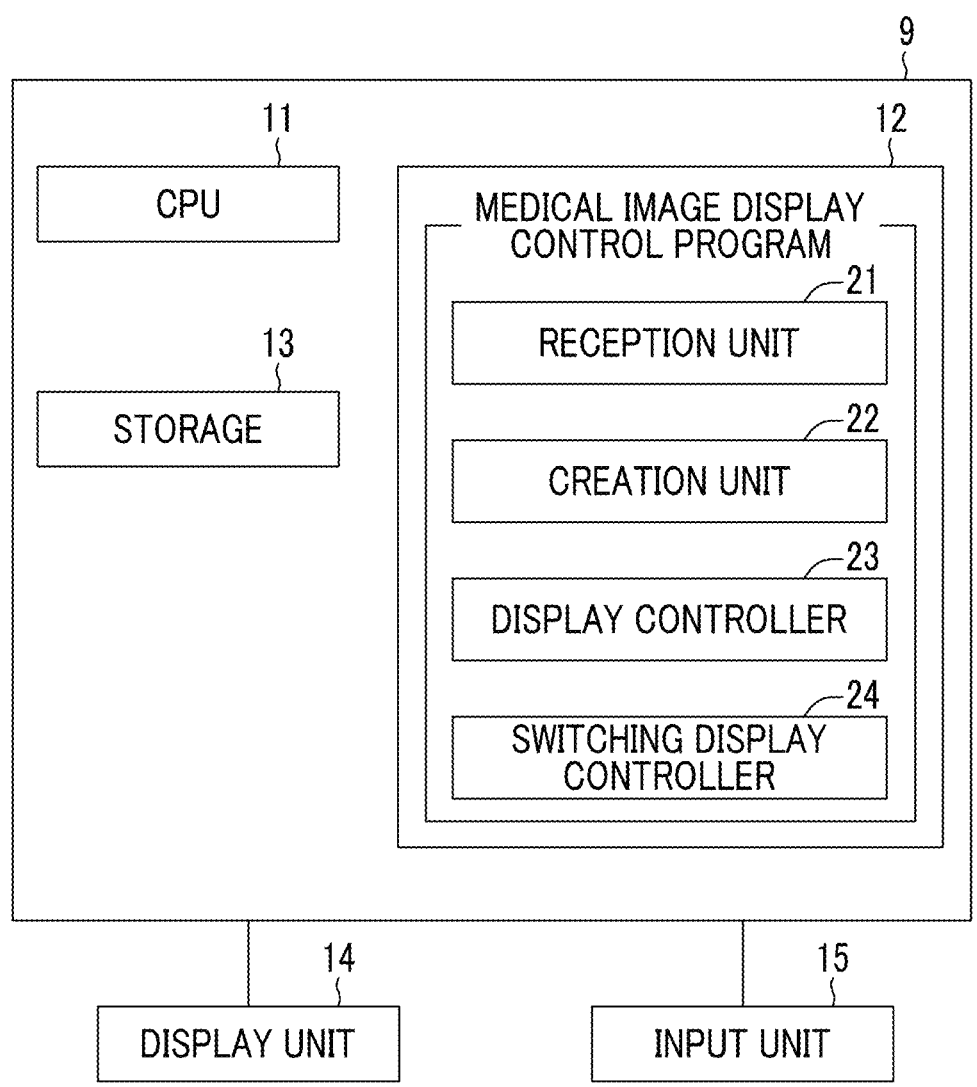
FIG. 2 is a schematic block diagram showing a configuration of a medical image display control device according to a first embodiment of the present disclosure.

FIG. 2 is a diagram showing a schematic configuration of the medical image display control device 9 according to the present embodiment which is realized by installing the medical image display control program on the computer. As shown in FIG. 2, the medical image display control device 9 includes a central processing unit (CPU) 11, a memory 12, and a storage 13. A display unit 14 such as a liquid crystal display and an input unit 15 such as a keyboard and a mouse are connected to the medical image display control device 9.

The storage 13 includes a storage device such as a hard disk or a solid state drive (SSD). The storage 13 stores various kinds of information including the medical images and information necessary for processing which are acquired from the medical information management server 5 via the network 10.

The memory 12 stores the medical image display control program. The medical image display control program defines, as processing to be executed by the CPU 11, reception processing of receiving an input instruction, creation processing of creating a new display image having a viewer region different from a viewer region of the display image displayed on the display unit 14 and a tab based on the received input instruction, which is processing of creating a display image having a tab and a viewer region in which at least a medical image is displayed, display control processing of performing control such that the tab of the created display image and the already displayed tab are displayed so as to be selectable on the display unit 14, and switching display control processing of performing control such that the viewer region corresponding to the selected tab is switched with the already displayed viewer region and is displayed on the display unit 14 in a case where any tab of the tabs displayed on the display unit 14 is selected.

The CPU 11 executes the processing according to the program, and thus, the computer functions as a reception unit 21, a creation unit 22, a display controller 23, and a switching display controller 24.

In a case where the interpretation WS 3 functions as a device that performs processing other than the medical image display control device 9, a program for executing this function is executed. For example, in a case where the medical image is analyzed, an analysis program is executed.

The reception unit 21 receives an input instruction from a user operating the input unit 15. The reception unit 21 receives the selection of the medical image of the patient to be displayed on the display unit 14 determined by the user by operating the input unit 15. In the present embodiment, the reception unit 21 includes a communication interface that communicates with the medical information management server 5 via the network 10, and also functions as an image acquisition unit that acquires the medical image to be displayed on the display unit 14 from the medical information database 6 via the medical information management server 5. In a case where the medical image is stored in the storage 13 in advance, the reception unit 21 may acquire the medical image stored in the storage 13. Other input instructions received by the reception unit 21 will be described in detail later.

The medical image acquired by the reception unit 21 also includes a medical image on which an analysis result using an analysis unit (not shown) or an analysis device provided outside the medical image display control device 9 is displayed.

Figure 3:
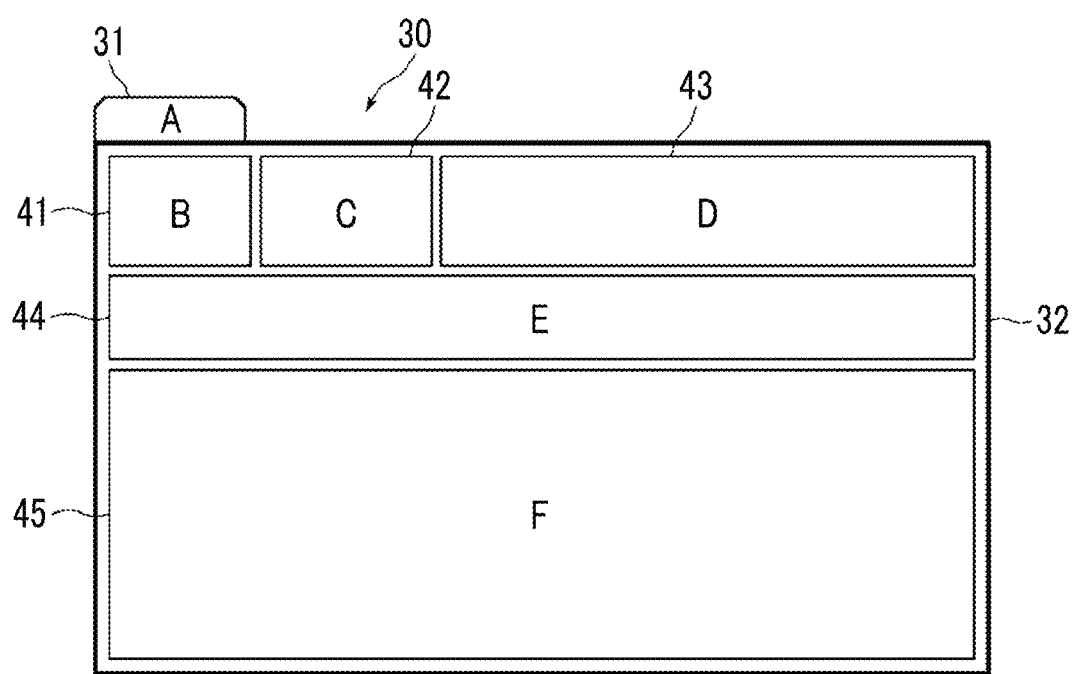
FIG. 3 is a diagram showing an example of a configuration of a display image.

The creation unit 22 creates a display image 30. FIG. 3 is a diagram showing an example of a configuration of the display image 30. As shown in FIG. 3, the display image 30 has tabs 31 shown in a region A, a patient information region 41 shown in a region B, an inspection list region 42 shown in a region C, a thumbnail display region 43 shown in a region D, a toolbar region 44 shown in a region E, and an image display region 45 shown in a region F. In the present embodiment, the patient information region 41, the inspection list region 42, the thumbnail display region 43, the toolbar region 44, and the image display region 45 constitute a viewer region 32 of the present disclosure.

In the present embodiment, the viewer region 32 includes the patient information region 41, the inspection list region 42, the thumbnail display region 43, the toolbar region 44, and the image display region 45, but the technology of the present disclosure is not limited thereto. The viewer region 32 may be, for example, the image display region 45 and the toolbar region 44 or may be the image display region 45 and the thumbnail display region 43 as long as the viewer region includes at least the image display region 45. The viewer region can be appropriately changed.

Figure 4:
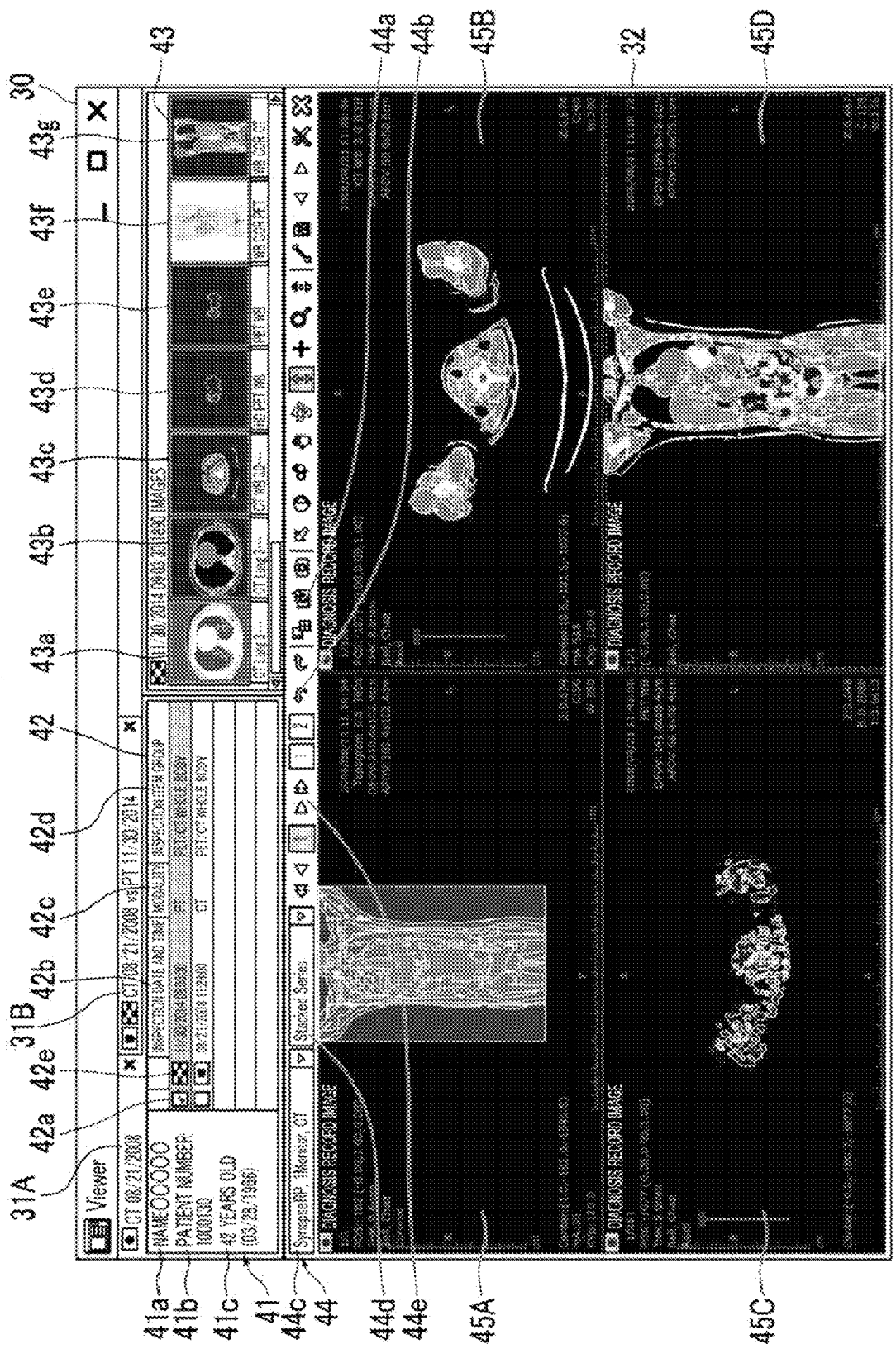
FIG. 4 is a diagram showing an example of a display screen.

FIG. 4 is a diagram showing an example of a display screen. In the present embodiment, FIG. 4 shows that a CT image is displayed as the medical image acquired in the current inspection. As shown in FIG. 4, a patient name 41a, a patient number 41b, and a patient age and birthday 41c are displayed in the patient information region 41. A list including check boxes 42a, an inspection date and time 42b, a modality 42c, an inspection item group 42d, and a mark 42e is displayed in the inspection list region 42. The mark 42e is identification information for identifying the medical image to be displayed in the viewer region 32, and is associated with each medical image. In the present embodiment, the mark 42e is set in a different aspect for each medical image acquired in one inspection.

In a case where the user checks the check box 42a, the reception unit 21 receives the selection of the medical image acquired in the checked inspection, acquires the received medical image, and the display controller 23 to be described later performs control such that the acquired medical image is displayed in the thumbnail display region 43 and the image display region 45.

Seven thumbnail images 43a to 43g obtained by reducing the medical images of the inspection of which the check boxes 42a are checked are displayed in the thumbnail display region 43. In a case where the number of medical images acquired in the inspection is more than 7, the display controller 23 displays the thumbnail images such that the thumbnail images to be displayed are changed by operating the scroll bar as shown in FIG. 4.

Various instruction buttons such as a snapshot button 44a, a back button 44b, a first pull-down menu 44c for selecting a layout of the display unit 14, and a second pull-down menu 44d for selecting a type of the medical image, for example, a type of the medical image acquired in one inspection, are displayed in the toolbar region 44. In the present embodiment, the reception unit 21 receives an input instruction associated with the instruction button such as an instruction using the pressed instruction button in a case where the instruction button is pressed, specifically, a snapshot instruction in a case where the snapshot button 44a is pressed, and an instruction to return the image display region 45 to a previous display state in a case where the back button 44b is pressed.

Medical images 45A to 45D selected by the user are displayed in the image display region 45. The selection by the user can be performed, for example, by selecting the thumbnail image displayed in the thumbnail display region 43. The medical image to be displayed as default can be set in advance by, for example, the number of the medical image. Although the number of medical images to be displayed in the image display region 45 is four in the present embodiment, the technology of the present disclosure is not limited thereto, and two images may be displayed or six images may be displayed. The number of images to be displayed can be changed as appropriate.

The creation unit 22 further creates a new display image having a viewer region different from the viewer region 32 of the display image 30 displayed on the display unit 14 based on the input instruction received by the reception unit 21 and a tab. Here, the layout of the "different viewer region" may be different, or the medical images to be displayed may be different. The new display image will be described in detail later.

The display controller 23 performs control such that various images are displayed on the display unit 14. In the present embodiment, the display controller 23 performs control such that the tab of the new display image created by the creation unit 22 and the already displayed tab are displayed so as to be selectable on the display unit 14.

Specifically, the display controller 23 displays a tab 31B of the new display image so as to be adjacent to a tab 31A already displayed on the display unit 14 as shown in FIG. 4.

In a case where any tab 31 is selected from the tabs 31 displayed on the display unit 14, the switching display controller 24 performs control such that the viewer region 32 corresponding to the selected tab 31 is switched with the already displayed viewer region 32 and is displayed on the display unit 14. For example, in the case of the display screen shown in FIG. 4, in a case where the tab 31B is selected in a state in which the tab 31A and the viewer region 32 corresponding to the tab 31A are displayed, the switching display controller 24 displays the viewer region corresponding to the selected tab 31B, that is, the viewer region different from the viewer region 32 of tab 31A on the display unit 14.

Next, a first embodiment of the new display image will be described. As shown in FIG. 4, in a state in which the display image 30 including the medical images 45A to 45D acquired in the current inspection is displayed on the display unit 14, in a case where the inspection using the positron emission tomography (PET) device is selected from the inspection list displayed in the inspection list region 42, that is, the check box 42a of the inspection using the PET device is checked, the display controller 23 displays the medical images acquired in the selected inspection in the thumbnail display region 43 as shown in FIG. 4.

For example, the medical image 45B to be compared is selected from the medical images displayed in the image display region 45, that is, the medical images 45A to 45D acquired in the current inspection, and the medical image to be compared, for example, the thumbnail image 43a displayed at a leftmost end, is further selected from the medical images displayed in the thumbnail display region 43, and in a case where a comparison instruction is received by the reception unit 21, the creation unit 22 creates the new display image corresponding to the comparison display.

Figure 5:
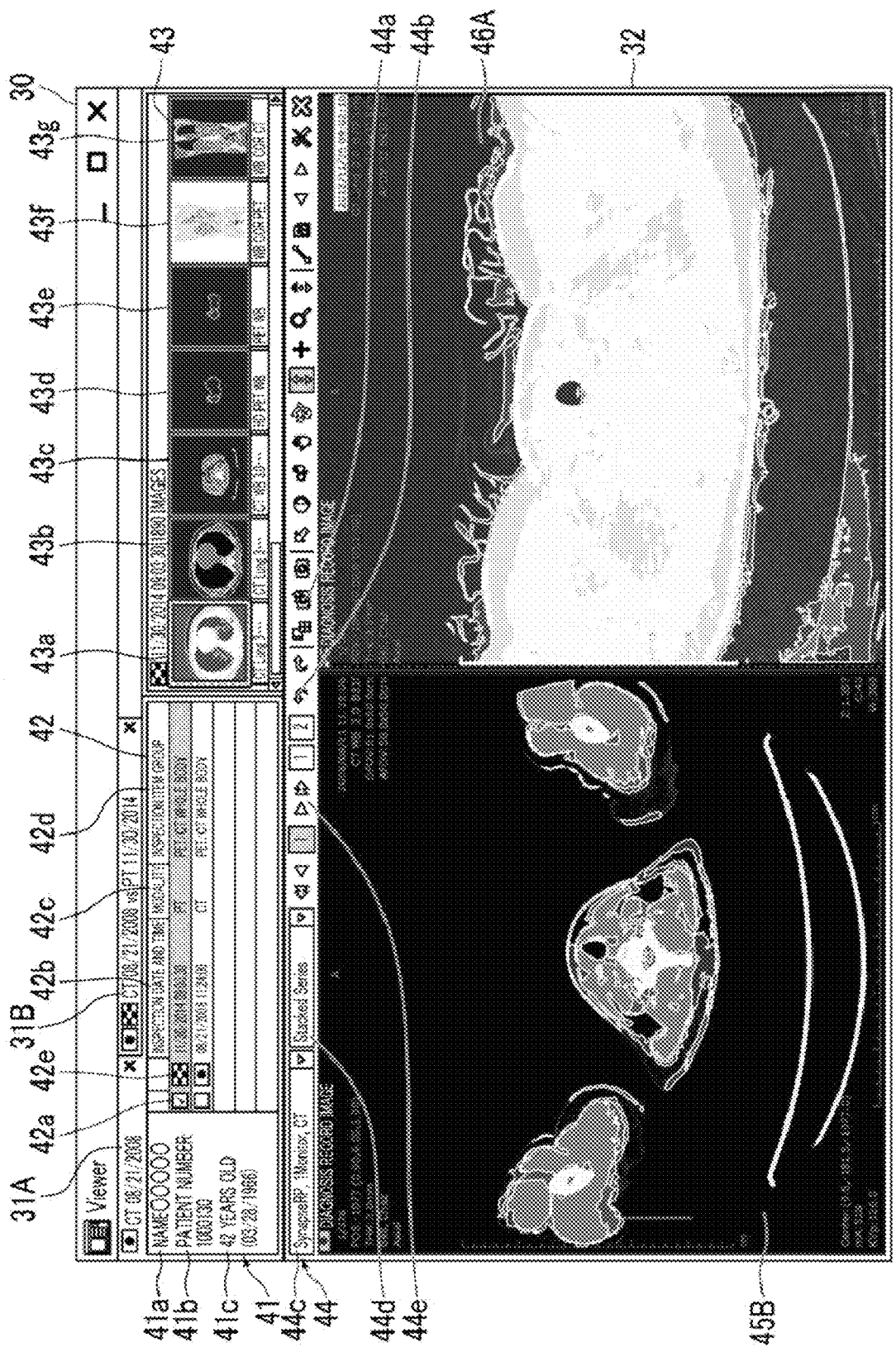
FIG. 5 is a diagram showing an example of a display screen during comparison display.

FIG. 5 is a diagram showing an example of a display screen at the time of comparison display. In a case where the reception unit 21 receives the comparison instruction, the display controller 23 displays the tab 31B of the new display image so as to be adjacent to the already displayed tab 31A on the display unit 14. Here, as for the comparison instruction, the comparison instruction is received by the reception unit 21 in a case where the inspection to be compared is double-clicked in the inspection list displayed in the inspection list region 42. In this case, the target to be interpreted is the current inspection, and the current inspection is compared with the double-clicked past inspection. In the present embodiment, since the medical image displayed in the thumbnail display region 43 is the image of the inspection displayed in the inspection list region 42, the inspection in which the medical image displayed in the thumbnail display region 43 is acquired is double-clicked, and thus, the reception unit 21 receives the comparison instruction.

In the technology of the present disclosure, the comparison instruction is not limited thereto. For example, in a case where the medical image to be compared from the medical images displayed in the thumbnail display region 43, for example, the thumbnail image 43a displayed at the leftmost end, is double-clicked, the reception unit 21 may receive the comparison instruction. In the inspection list region 42, in a case where the user checks the plurality of inspections, displays a menu by right-clicking the mouse, and selects a comparison start item displayed in the menu, the reception unit 21 may receive the comparison instruction.

Identification information for identifying the medical image to be displayed in each viewer region is displayed on the tabs 31A and 31B. In the present embodiment, as the identification information, the mark 42e to be displayed in the inspection list region 42, the modality 42c displayed in the inspection list region 42, and an inspection date and time displayed in the inspection date and time 42b are displayed as character information related to the medical image displayed in each viewer region.

Specifically, a mark with a circle in a frame and "CT 08/21/2008" are displayed on the tab 31A. A mark with a circle in a frame, a mark with a grid pattern in a frame, and "CT 08/21/2008 vs PT 11/30/2014" are displayed on the tab 31B. As stated above, the identification information for identifying the medical image to be displayed on the tab 31 is displayed, and thus, the user can easily recognize what kind of medical image the medical image to be displayed in the viewer region 32 corresponding to the tab 31 is.

The switching display controller 24 switches the viewer region corresponding to the tab 31B of the new display image with the already displayed viewer region 32 and displays the switched viewer region on the display unit 14. As shown in FIG. 5, in the viewer region corresponding to the tab 31B, the medical image 45B acquired in the current inspection is displayed on a left side, and the medical image 46A corresponding to the thumbnail image 43a selected in the thumbnail display region 43 is displayed on a right side of the image display region 45. As shown in FIG. 5, a portion to be compared is enlarged and displayed in the medical image 46A.

Two medical images are displayed for comparative display in the present embodiment, but the technology of the present disclosure is not limited thereto. The number of medical images can be randomly set in advance such that any number of medical images such as three or four images can be displayed to be comparable.

In the case of the display method of the related art in which the tabs are not displayed, at the time of performing the comparison display, a state in which the image acquired in the current inspection is displayed is changed to the layout for the comparison display. Thus, in order to return to the immediately previous display, it is necessary to store the immediately previous display state. In a case where the next comparison display is desired, an instruction from the user needs to be received to display in a first comparison display state or to display in the previous comparison display state, and the user needs to search for a desired comparison display state by pressing, for example, the back button 44b multiple times while checking the display screen.

In the present embodiment, the new display image having the tab and the viewer region is created, and the viewer region corresponding to the tab selected according to the selection of the tab is switched with the already displayed viewer region, and is displayed on the display unit 14. Accordingly, in a case where the interpretation of the medical image acquired in the current inspection is desired, it is possible to view the display state of the state before the comparison display is performed by merely selecting the tab displaying the identification information for identifying the medical image acquired in the current inspection. In a case where this state is returned to the state of the comparison display again, it is possible to view the desired comparison display state by merely selecting the tab displaying the identification information for identifying the medical image on which the desired comparison display is performed.

Accordingly, since the desired display state can be viewed by merely selecting the tab on which the identification information for identifying the desired medical image is displayed, the time and effort of the operation by the user are reduced, and the efficiency of the operation can be improved. Since the medical images to be compared can be simultaneously displayed on one screen with the same size, the medical images can be easily observed.

Since the viewer region being viewed is merely switched and displayed by selecting the tab, the display state such as a gradation, a magnification ratio, and a page position in the display image 30 created by the creation unit 22 can be maintained without being changed.

Next, a second embodiment of the new display image will be described. For example, in a case where an image series including the plurality of medical images is acquired in one inspection, in a state in which the display image 30 including the medical images 45A to 45D acquired in the current inspection is displayed on the display unit 14, it is assumed that the image series is selected by the second pull-down menu 44*d* displayed in the toolbar region 44 as shown in FIG. 4. The creation unit 22 creates the new display images, each including the viewer region in which the plurality of medical images of the image series are displayed, by a predetermined number of images the number of images corresponding to the plurality of medical images.

Figure 6:
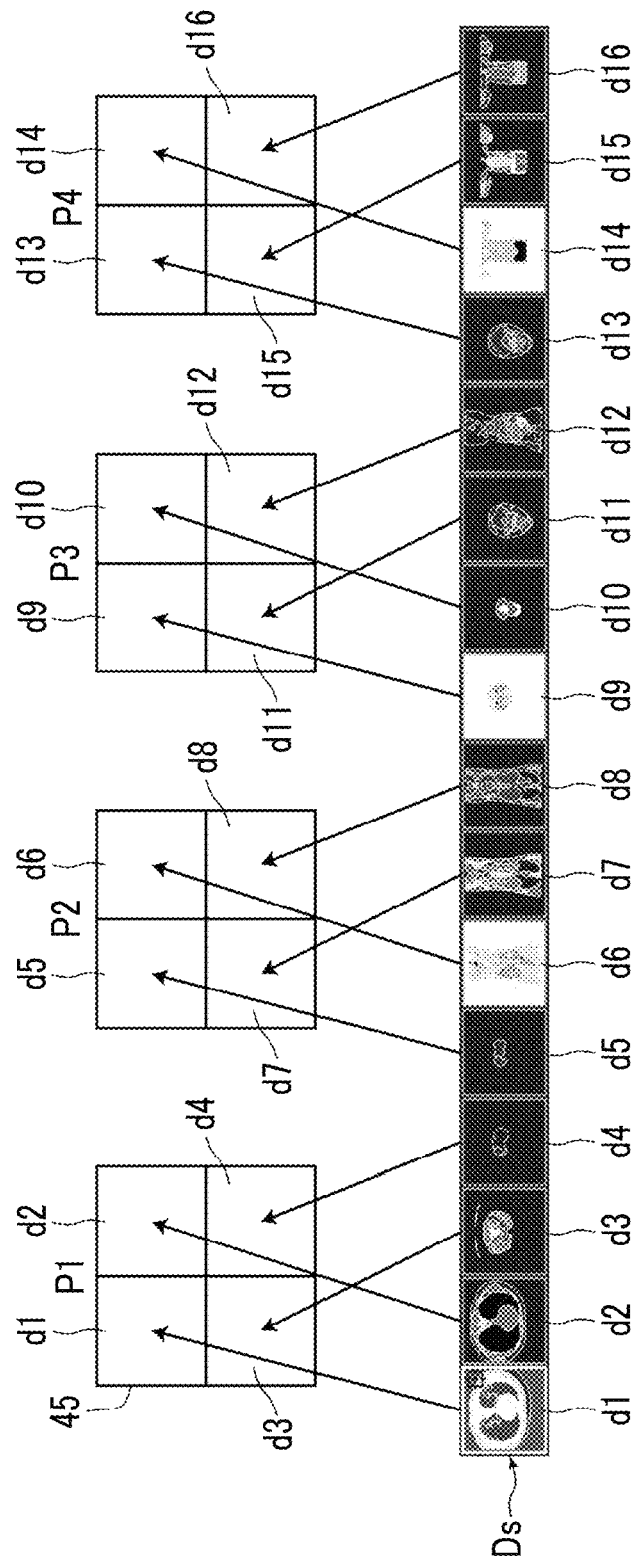
FIG. 6 is a diagram illustrating a configuration of a display image at the time of displaying an image series.

FIG. 6 is a diagram illustrating a configuration of the display image at the time of displaying the image series. As shown in a lower part of FIG. 6, it is assumed that an image series Ds including 16 medical images of, for example, medical images d1 to d16 is acquired in one inspection. In a case where the medical images are arranged in two columns vertically and two rows horizontally, that is, in a 2×2 layout in the image display region 45, and the image series is selected by the second pull-down menu 44*d*, the creation unit 22 generates four display images on which four medical images are arranged in the image display region 45.

In the present embodiment, the creation unit 22 displays a first display image in which the medical images d1 to d4 of a page P1 are displayed in the image display region 45, a second display image in which the medical images d5 to d8 of a page P2 are displayed in the image display region 45, a third display image in which the medical images d9 to d12 of a page P3 are displayed in the image display region 45, and a fourth display image in which the medical images d13 to d16 of a page P4 are displayed in the image display region 45. The mark 42*e* to be displayed in each inspection list region 42, the character information related to the medical image to be displayed in each viewer region, and a page number are displayed on each tab 31 of the first to fourth display images.

The display controller 23 displays the created first display image on the display unit 14, and displays each tab and the tab of the first display image so as to be selectable on the display unit 14 by using the created second to fourth display images as the new display images.

In a case where any tab of the second to fourth display images is selected, the switching display controller 24 switches the viewer region 32 of the display image corresponding to the selected tab with the already displayed viewer region on the display unit 14.

In the display method of the related art in which the tabs are not displayed, the pages to be displayed in the order of pages P1, P2, P3, and P4 are switched by pressing a forward button 44*e* displayed in the toolbar region 44. Thus, in a case where the page P4 is desired to be viewed in a state in which the page P1 is displayed, it is necessary to press the forward button 44*e* three times.

In the present embodiment, in a case where the page P4 is desired to be viewed in a state in which the page P1 is displayed, since the user can easily switch to a state in which the page P4 is displayed by merely selecting the tab on which 4, which is the page number of the page P4, is displayed, the time and effort of the operation by the user are reduced, and thus, the efficiency of the operation can be improved. Since the layouts can be equal for the tabs, the display sizes of the medical images can be equal, and the medical image can be easily observed.

Next, a third embodiment of the new display image will be described. For example, it is assumed that the medical image display control device 9 has a snapshot function. Here, the snapshot function is a function capable of restoring the display state in which the display screen is displayed by generating and storing, as a snapshot, restoration information capable of restoring the display state in which the current display screen is displayed and referring to the stored restoration information, that is, the snapshot.

In the present embodiment, in a case where the snapshot button 44*a* displayed in the toolbar region 44 is pressed in a state in which the viewer region 32 in the display state desired by the user is displayed on the display unit 14, the creation unit 22 creates the new display image including the displayed viewer region 32 as shown in FIG. 4. Whenever the snapshot button 44*a* is pressed, the creation unit 22 creates the new display image including the viewer region 32 displayed on the display unit 14 immediately before a timing at which the snapshot button 44*a* is pressed.

Figure 7:
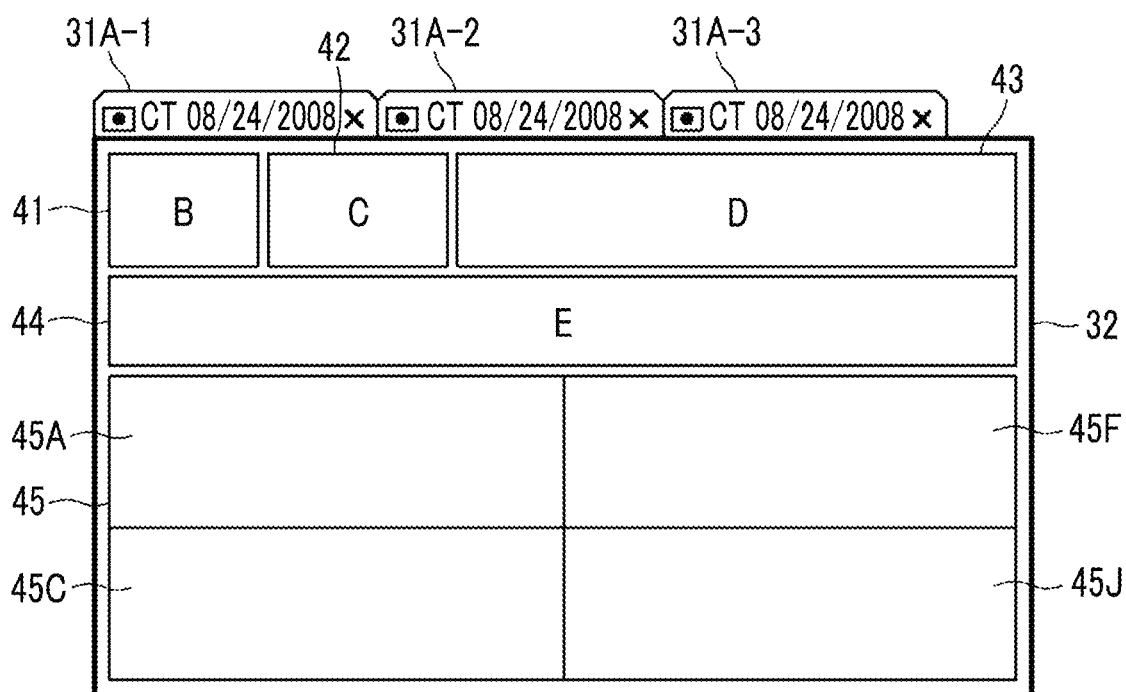
FIG. 7 is a diagram illustrating identification information of a tab.

FIG. 7 is a diagram illustrating the identification information of the tab. As shown in FIG. 7, the display controller 23 displays tabs 31A-2 and 31A-3 of the new display image and a tab 31A-1 of the already displayed display image whenever the new display image is created so as to be selectable on the display unit 14.

In a case where any of the tabs 31A-1 to 31A-3 is selected, the switching display controller 24 switches the viewer region 32 of the display image corresponding to the selected tab with the already displayed viewer region and displays the switched viewer region on the display unit 14.

In the case of the display method of the related art in which the tabs are not displayed, the display state of the medical image which is a point in one inspection is saved as the snapshot multiple times, and the saved snapshot is restored and reviewed later. At this time, the saved snapshot is selected, and the display state of the viewer region 32 is restored based on the display state displayed in the selected snapshot. That is, in order to view the plurality of snapshots, the above processing is performed in sequence, and thus, it takes time.

In the present embodiment, in a case where the snapshot is desired to be viewed, since the user can switch to a different snapshot by merely selecting the tab, the time required to view the plurality of snapshots can be reduced. Accordingly, the time and effort of the operation by the user are reduced, and thus, the efficiency of the operation can be improved.

The network 10 is a wired or wireless local area network for connection with various devices in a hospital. In a case where the interpretation WS 3 and the clinical department WS 4 are installed in another hospital or clinic, the network 10 may have a configuration in which local area networks of the hospitals are connected to each other via the Internet or a dedicated line.

Figure 8:
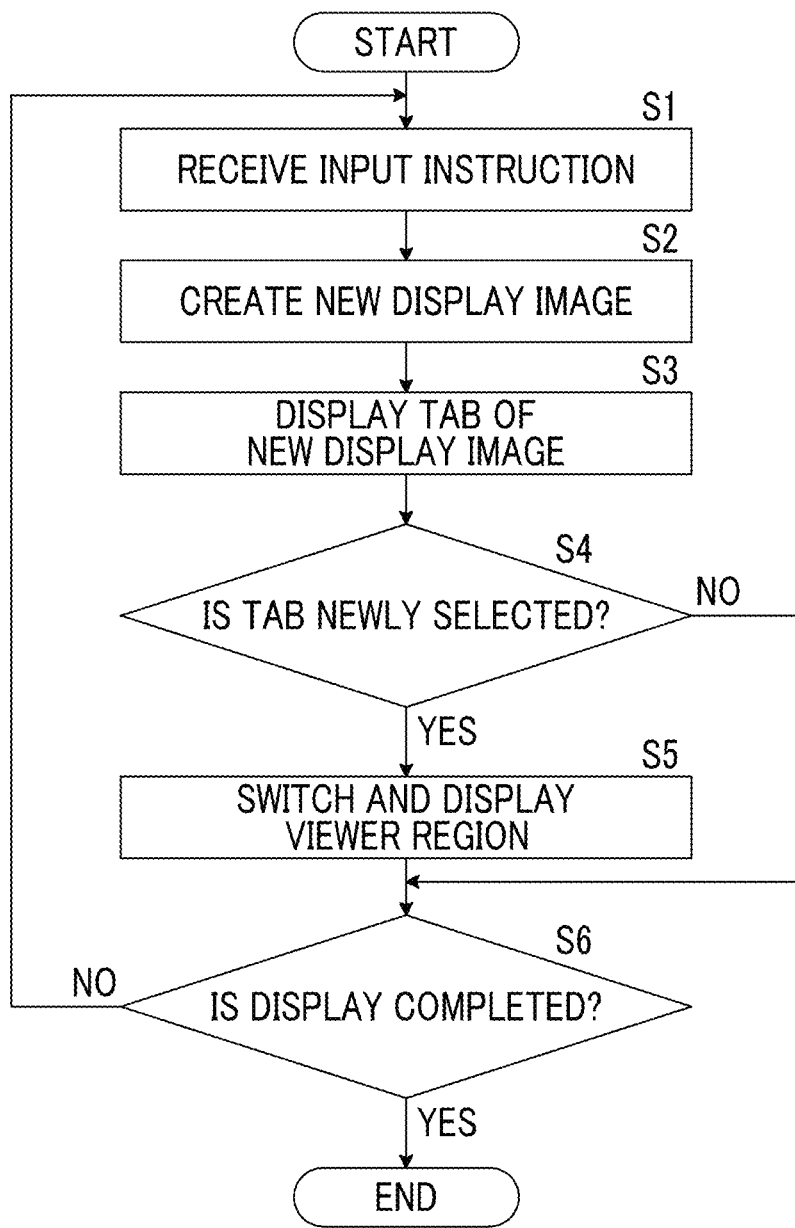
FIG. 8 is a flowchart showing processing performed in the first embodiment of the present disclosure.

Next, processing performed in the present embodiment will be described. FIG. 8 is a flowchart showing processing performed by the medical image display control device 9 included in the interpretation WS 3 in the present embodiment. First, the reception unit 21 receives, as the target to be displayed in the image display region, any input instruction of the input instructions to acquire the medical image of the patient, the input instruction to perform the comparison display, the input instruction to display the image series, and the input instruction to display the snapshot (step S1). Specifically, in a case where the patient is selected, that is, in a case where the patient information is displayed in the patient information region 41, the input instruction to acquire the medical image of the patient is considered to have been received, and the medical image corresponding to the inspection displayed in the inspection list region 42 is acquired. In a case where the inspection to be compared is double-clicked in the inspection list displayed in the inspection list region 42, the input instruction to perform the comparison display is received. In a case where the image series is selected by the second pull-down menu 44d, the input instruction to display the image series is received. In a case where the snapshot button 44a is pressed, the input instruction to display the snapshot is received.

Subsequently, the creation unit 22 creates the new display image as described above based on the content of the input instruction (step S2). The display controller 23 displays the tab of the created new display image as shown in FIGS. 4, 5, and 7 (step S3). Subsequently, the CPU 11 determines whether or not the tab is newly selected (step S4), and in a case where the tab is newly selected (step S4; YES), the switching display controller 24 switches the viewer region corresponding to the selected tab with the already displayed viewer region and displays the switched viewer region (step S5).

Subsequently, the CPU 11 determines whether or not the series of display controls using the display controller 23 is completed, that is, whether or not the display on the display unit 14 is completed (step S6), and in a case where it is determined that the display is completed (step S6; YES), the series of processing performed by the medical image display control device 9 is completed. On the other hand, in a case where it is determined in step S6 that the display is not completed (step S6; NO), the CPU 11 shifts the processing to step S1 and repeats the subsequent processing. In a case where the CPU 11 determines that the tab is not newly selected in step S4 (step S4; NO), the CPU 11 shifts the processing to step S6 and repeats the subsequent processing. By doing this, the processing using the medical image display control device 9 is performed.

As described above, in the present embodiment, the control is performed such that the input instruction is received, the new display image having the tab and the viewer region different from the viewer region 32 of the display image 30 having the tab 31 and the viewer region 32 on which at least the medical image is displayed which is displayed on the display unit 14 based on the received input instruction is created, the tab of the created new display image and the already displayed tab are displayed so as to be selectable on the display unit, and the viewer region corresponding to the selected tab is switched with the already displayed viewer region and is displayed on the display unit in a case where any tab of the tabs displayed on the display unit 14 is selected. Accordingly, the user merely selects the tab, and thus, the viewer region in which the medical image is displayed can be switched to the viewer region different from this viewer region and displayed. Therefore, the time and effort of the operation by the user are reduced, and thus, the efficiency of the operation can be improved. In a case where the layouts for the tabs are the same layout, it is possible to easily compare and observe the medical images for the tabs in a case where the viewer region is switched and displayed.

In the present embodiment, since the patient information, the inspection list, the thumbnail images, the toolbar, and the medical images are displayed in the viewer region 32, the selection of the patient, the selection of the inspection list, the selection of the thumbnail images, the selection of the images, and various input instructions can be performed for each selected tab. Accordingly, since the same processing can be performed for each selected tab, that is, even though any tab is selected, the operability by the user is improved.

Figure 9:
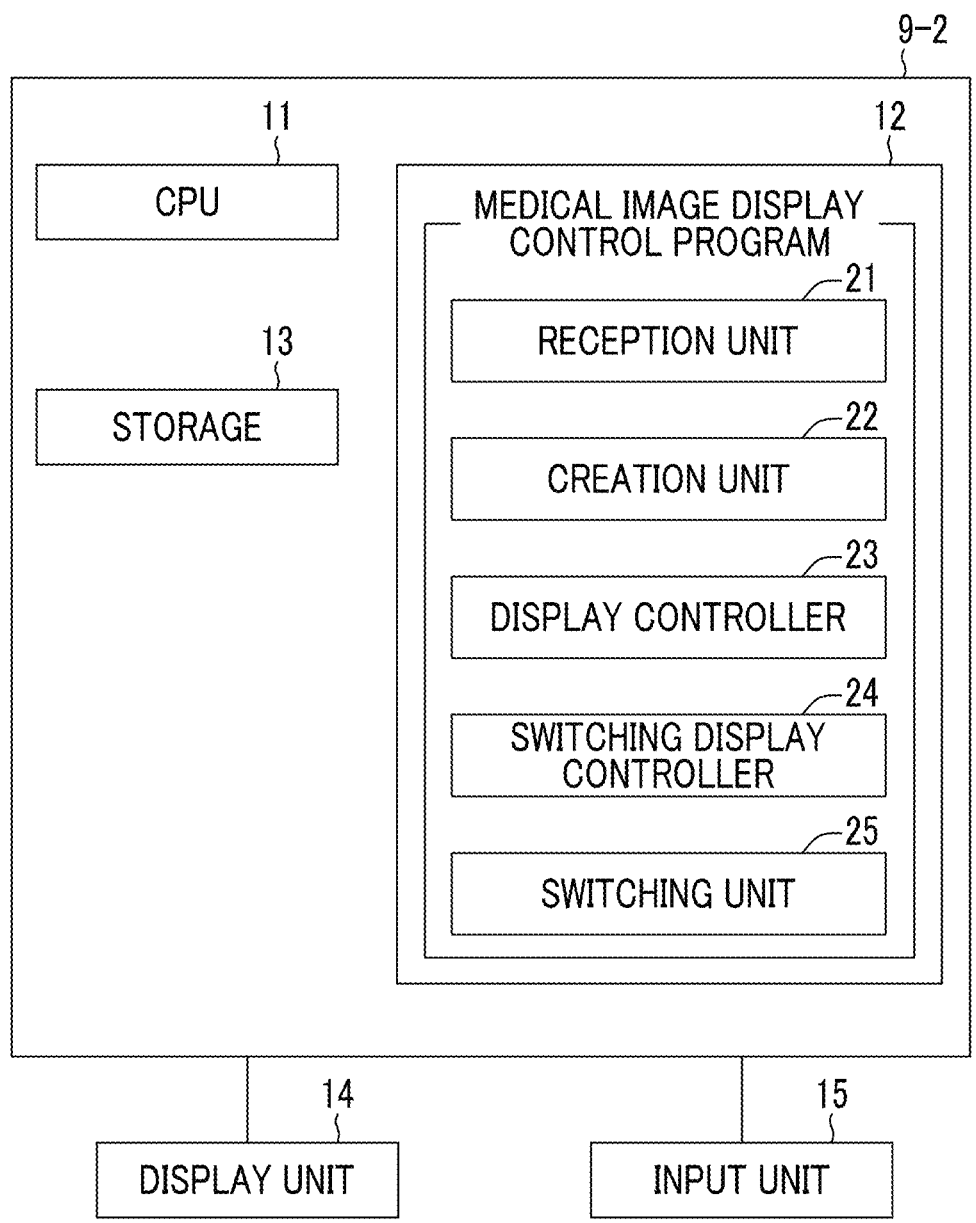
FIG. 9 is a schematic block diagram showing a configuration of a medical image display control device according to a second embodiment of the present disclosure.

Next, a medical image display control device 9-2 of a second embodiment will be described below. FIG. 9 is a schematic block diagram showing a configuration of the medical image display control device 9-2 according to the second embodiment of the present disclosure. In FIG. 9, since the same parts as those of the medical image display control device 9 shown in FIG. 2 are indicated by the same references, the description thereof is omitted here, and only the different parts will be described in detail.

As shown in FIG. 9, the medical image display control device 9-2 of the second embodiment includes a switching unit 25. In a case where the same medical image is displayed in the selection of any tab of the plurality of tabs, the switching unit 25 switches between whether or not to apply image processing on the same medical image to be displayed in the first tab to the same medical image to be displayed in the selection of a tab other than the first tab.

Specifically, in a case where the switching unit 25 selects to apply, image processing such as brightness, contrast, slice movement, enhancement, and sharpness is similarly performed on the medical image 45B displayed in the viewer region 32 corresponding to the tab 31A as shown in FIG. 4 and the medical image 45B displayed in the viewer region 32 corresponding to the tab 31B as shown in FIG. 5.

On the other hand, in a case where the switching unit 25 selects not to apply, different image processing is performed on the medical image 45B shown in FIG. 4 and the medical image 45B shown in FIG. 5.

The setting using the switching unit 25 can be selected in advance by the user, but the technology of the present disclosure is not limited thereto. The switching unit 25 may be controlled to automatically switch between whether or not to apply, for example, based on any condition.

Figure 10:
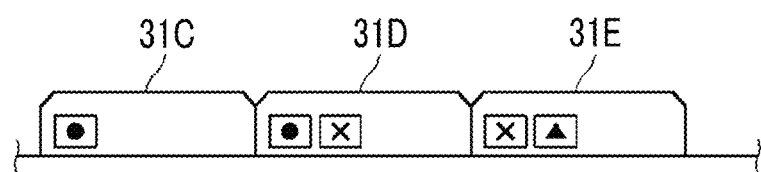
FIG. 10 is a diagram showing an example of identification information.

In the above-described embodiment, the character information indicating the information related to the medical image, such as the inspection date and the inspection item, is displayed as identification information on the tab 31 in addition to the mark 42e associated with each medical image, but the technology of the present disclosure is not limited thereto. FIG. 10 is a diagram showing an example of the identification information. As shown in FIG. 10, only the mark 42e may be displayed on the tab 31C to the tab 31E as the identification information. In this case, it is possible to easily recognize which medical image is displayed in the viewer region 32 corresponding to the tab 31. For example, in a case where the comparison display is performed, it is possible to easily check which tab 31 is selected to display which medical image is comparatively displayed.

In the present embodiment, the mark 42e has the aspects shown in FIGS. 4 and 5, but the technology of the present disclosure is not limited thereto. The mark 42e may be, for example, a shape simply representing a part to be inspected, or may be a part of character information representing the part to be inspected. Alternatively, a different color may be assigned to each medical image and displayed, or the color of the medical image can be set as appropriate.

In the above embodiment, the medical image display control program according to the present embodiment may be installed in the clinical department WS 4. In this case, the above-mentioned display method is applied in the clinical department WS 4.

In the above embodiment, a dedicated terminal for executing the medical image display control program according to the present embodiment may be separately installed as the medical image display control device. In this case, the display image created by the separately installed medical image display control device is registered in the medical information database 6, and is used to display the display image in the interpretation WS 3, the clinical department WS 4, and the like.

In each of the above-described embodiments, the following various processors can be used as a hardware structure of processing units that execute various kinds of processing such as the reception unit 21, the creation unit 22, the display controller 23, the switching display controller 24, and the switching unit 25. As described above, in addition to the CPU which is a general-purpose processor that functions as various processing units by executing software (programs), the various processors include a programmable logic device (PLD), which is a processor capable of changing a circuit configuration after manufacture, such as a field programmable gate array (FPGA), and a dedicated electrical circuit, which is a processor having a circuit configuration specifically designed in order to execute specific processing such as an application specific integrated circuit (ASIC).

One processing unit may be constituted by one of these various processors, or may be constituted by a combination of two or more processors of the same type or different types (for example, a combination of a plurality of FPGAs or a combination of a CPU and an FPGA). The plurality of processing units may be constituted by one processor.

As an example in which the plurality of processing units are constituted by one processor, firstly, one processor is constituted by a combination of one or more CPUs and software as represented by computers such as clients and servers, and this processor functions as the plurality of processing units. Secondly, a processor that realizes the functions of the entire system including the plurality of processing units via one integrated circuit (IC) chip is used as represented by a system on chip (SoC). As described above, the various processing units are constituted by using one or more of the various processors as the hardware structure.

More specifically, an electric circuitry in which circuit elements such as semiconductor elements are combined can be used as the hardware structure of these various processors.

EXPLANATION OF REFERENCES

1: medical information system
2: modality
3: interpretation workstation
4: clinical department workstation
5: medical information management server
6: medical information database
7: interpretation report server
8: interpretation report database
9: medical image display control device
10: network
11: CPU
12: memory
13: storage
14: display unit
15: input unit
21: reception unit
22: creation unit
23: display controller
24: switching display controller
25: switching unit
30: display image
31: tab
32: viewer region
41: patient information region
41a: name
41b: patient number
41c: birthday
42: inspection list region
42a: check box
42b: inspection date and time
42c: modality
42d: inspection item group
42e: mark
43: thumbnail display region
43a: thumbnail image
44: toolbar region
44a: snapshot button
44b: back button
44c: first pull-down menu
44d: second pull-down menu
44e: forward button
45: image display region
45A: medical image
45B: medical image
46A: medical image

What is claimed is:

1. A medical image display control device comprising:
a processor, configured to:
create a display image having a tab and a viewer region in which at least a medical image is displayed, wherein the tab of the display image comprises character information and at least one icon representing identification information for identifying a type of the medical image, wherein the character information comprises an inspection date and time at which the medical image is generated;
perform control such that the display image is displayed on the display;
receive an input instruction;
create a new display image having a tab and a viewer region different from the viewer region of the display image displayed on a display based on the input instruction, wherein the tab of the new display image comprises new character information and at least one new icon representing new identification information for identifying a type of the new medical image, wherein the at least one new icon is different from the at least one icon, and wherein the new character information is different from the character information and comprises a new inspection date and time at which the new medical image is generated, wherein the at least one new icon includes a first icon and a second icon having a different pattern as compared to the first icon, and the first icon represents a first type of medical image different from a second type of medical image represented by the second icon;
perform control such that the tab of the new display image is displayed along with the already displayed tab in response to the new display image being created so as to be selectable on the display; and perform control such that in a case where any tab of the tabs displayed on the display is selected, the viewer region corresponding to the selected tab is switched with the already displayed viewer region and is displayed on the display.

2. The medical image display control device according to claim 1, wherein the viewer region includes an image display region in which the medical image is displayed and at least one or more regions of a patient information region in which information regarding a patient is displayed, an inspection list region in which information regarding each inspection is displayed for each inspection, a thumbnail display region in which the medical image acquired in one inspection is reduced and displayed, or a toolbar region in which a plurality of input instruction buttons are displayed.

3. The medical image display control device according to claim 2, wherein the processor is further configured to:

in a case where the same medical image is displayed both in the view region corresponding to the already displayed tab and the viewer region corresponding to the tab of the new display image, switch between whether or not to apply image processing on the same medical image displayed in the view region corresponding to the already displayed tab to the same medical image displayed in the viewer region corresponding to the tab of the new display image.

4. The medical image display control device according to claim 2, wherein, in a case where the processor receives an input instruction related to two or more medical images, the processor creates the new display images, each including a viewer region in which the two or more medical images are displayed so as to be comparable.

5. The medical image display control device according to claim 2, wherein, in a case where the processor receives an input instruction related to an image series including a plurality of medical images acquired in one inspection, the processor creates the new display images, each including a viewer region in which the plurality of medical images of the image series are displayed by a predetermined number of images, the number of the new display images corresponding to the plurality of medical images.

6. The medical image display control device according to claim 2, wherein, in a case where the processor receives an input instruction related to a snapshot function of storing the viewer region in a state in which a display state is restorable such that the viewer region is stored by the snapshot function, the processor creates a new display image including the stored viewer region.

7. The medical image display control device according to claim 1, wherein the processor is further configured to:

in a case where the same medical image is displayed both in the view region corresponding to the already displayed tab and the viewer region corresponding to the tab of the new display image, switch between whether or not to apply image processing on the same medical image displayed in the view region corresponding to the already displayed tab to the same medical image displayed in the viewer region corresponding to the tab of the new display image.

8. The medical image display control device according to claim 7, wherein, in a case where the processor receives an input instruction related to two or more medical images, the processor creates the new display images, each including a viewer region in which the two or more medical images are displayed so as to be comparable.

9. The medical image display control device according to claim 7, wherein, in a case where the processor receives an input instruction related to an image series including a plurality of medical images acquired in one inspection, the processor creates the new display images, each including a viewer region in which the plurality of medical images of the image series are displayed by a predetermined number of images, the number of the new display images corresponding to the plurality of medical images.

10. The medical image display control device according to claim 7, wherein, in a case where the processor receives an input instruction related to a snapshot function of storing the viewer region in a state in which a display state is restorable such that the viewer region is stored by the snapshot function, the processor creates a new display image including the stored viewer region.

11. The medical image display control device according to claim 1, wherein, in a case where the processor receives an input instruction related to two or more medical images, the processor creates the new display images, each including a viewer region in which the two or more medical images are displayed so as to be comparable.

12. The medical image display control device according to claim 1, wherein, in a case where the processor receives an input instruction related to an image series including a plurality of medical images acquired in one inspection, the processor creates the new display images, each including a viewer region in which the plurality of medical images of the image series are displayed by a predetermined number of images, the number of the new display images corresponding to the plurality of medical images.

13. The medical image display control device according to claim 1, wherein, in a case where the processor receives an input instruction related to a snapshot function of storing the viewer region in a state in which a display state is restorable such that the viewer region is stored by the snapshot function, the processor creates a new display image including the stored viewer region.

14. The medical image display control device according to claim 1, wherein the processor displays a list of medical image thumbnails for inspection, and wherein the input instruction further includes the new medical image included in the list of medical image thumbnails being selected by the user.

15. The medical image display control device according to claim 14, wherein the processor displays a list of medical images that includes a plurality of check boxes, and wherein the input instruction further includes a check box, among the plurality of check boxes, corresponding to the new medical image being checked by the user.

16. The medical image display control device according to claim 1,
- wherein the character information further comprises information of a device that generates the medical image, and
- wherein the new character information further comprises information of another device that generates the new medical image.

17. A medical image display control method comprising:
- creating a display image having a tab and a viewer region in which at least a medical image is displayed, wherein the tab of the display image comprises character information and at least one icon representing identification information for identifying a type of the medical image, wherein the character information comprises an inspection date and time at which the medical image is generated;
- performing control such that the display image is displayed on the display;
- receiving an input instruction;
- creating a new display image having a tab and a viewer region different from the viewer region of the display image displayed on a display based on the received input instruction, wherein the tab of the new display image comprises new character information and at least one new icon representing new identification information for identifying a type of the new medical image, and wherein the new character information is different from the character information and comprises a new inspection date and time at which the new medical image is generated, wherein the at least one new icon includes a first icon and a second icon having a different pattern as compared to the first icon, and the first icon represents a first type of medical image different from a second type of medical image represented by the second icon;
- displaying the tab of the created new display image along with the already displayed tab in response to the new display image being created so as to be selectable on the display; and
- performing control such that in a case where any tab of the tabs displayed on the display is selected, the viewer region corresponding to the selected tab is switched with the already displayed viewer region and is displayed on the display.

18. A non-transitory computer readable recording medium storing a medical image display control program causing a computer to execute a procedure of:
- creating a display image having a tab and a viewer region in which at least a medical image is displayed, wherein the tab of the display image comprises character information and at least one icon representing identification information for identifying a type of the medical image, wherein the character information comprises an inspection date and time at which the medical image is generated;
- performing control such that the display image is displayed on the display;
- receiving an input instruction;
- creating a new display image having a tab and a viewer region different from the viewer region of the display image displayed on a display based on the received input instruction, wherein the tab of the new display image comprises new character information and at least one new icon representing new identification information for identifying a type of the new medical image, wherein the at least one new icon is different from the at least one icon, and wherein the new character information is different from the character information and comprises a new inspection date and time at which the new medical image is generated, wherein the at least one new icon includes a first icon and a second icon having a different pattern as compared to the first icon, and the first icon represents a first type of medical image different from a second type of medical image represented by the second icon;
- displaying the tab of the created new display image along with the already displayed tab in response to the new display image being created so as to be selectable on the display; and
- performing control such that in a case where any tab of the tabs displayed on the display is selected, the viewer region corresponding to the selected tab is switched with the already displayed viewer region and is displayed on the display.

* * * * *